United States Patent [19]

Lebing et al.

[11] Patent Number: 5,610,285
[45] Date of Patent: Mar. 11, 1997

[54] PURIFICATION OF α-1 PROTEINASE INHIBITOR USING NOVEL CHROMATOGRAPHIC SEPARATION CONDITIONS

[75] Inventors: Wytold R. Lebing; Sharon X. Chen, both of Raleigh, N.C.

[73] Assignee: Bayer Corporation, Berkeley, Calif.

[21] Appl. No.: 295,119

[22] Filed: Aug. 24, 1994

[51] Int. Cl.$^6$ .......................... C07K 1/16; C07K 14/435; A61K 35/14

[52] U.S. Cl. .......................... 530/416; 530/380; 530/392; 530/395; 530/830

[58] Field of Search .................... 530/380, 381, 530/395, 392, 416, 829, 830, 831; 514/12, 21

[56] References Cited

U.S. PATENT DOCUMENTS

| | | | |
|---|---|---|---|
| 3,293,236 | 12/1966 | Schultze | 530/392 |
| 4,379,087 | 4/1983 | Coan et al. | 530/380 |
| 4,629,567 | 12/1986 | Bollen et al. | 210/635 |
| 4,656,254 | 4/1987 | Shearer et al. | 530/393 |
| 4,752,576 | 6/1988 | Brake et al. | 435/69.2 |
| 5,319,072 | 6/1994 | Uemora et al. | 530/393 |

*Primary Examiner*—Mindy Fleisher
*Assistant Examiner*—Nancy J. Degen
*Attorney, Agent, or Firm*—James A. Giblin

[57] ABSTRACT

Cation chromatography with solutions at pH less than 6.0 and low ionic strength can be utilized to purify human α-1 proteinase inhibitor (α-1 PI) from biological fluids including plasma and plasma fractions. The cation chromatography takes advantage of the fact that active α-1 PI does not bind to the cation column under these conditions but other proteins, including denatured α-1 PI and albumin, do. The effect is that active α-1 PI flows through the chromatography column leaving the contaminating proteins behind. Recovery of α-1 PI is high and improvement of purity is dramatic.

4 Claims, 3 Drawing Sheets

FR IV – 1 PASTE SUSPENSION

ANION EXCHANGE CHROMATOGRAPHY

CATION EXCHANGE FLOW THROUGH CHROMATOGRAPHY

VIRAL INACTIVATION STEP(S)

CATION EXCHANGE FLOW THROUGH CHROMATOGRAPHY

STERILE FILTER

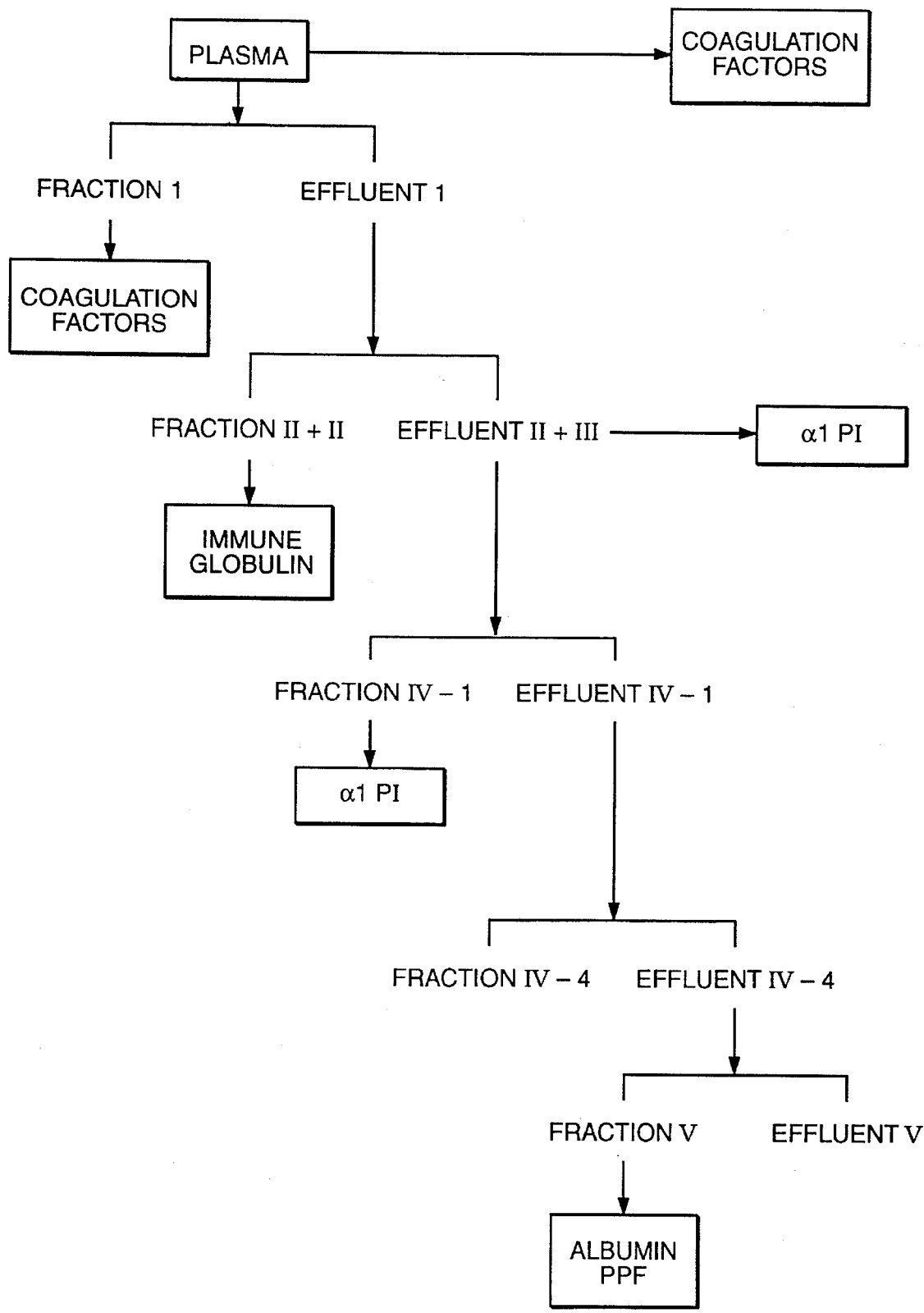
FIG._1

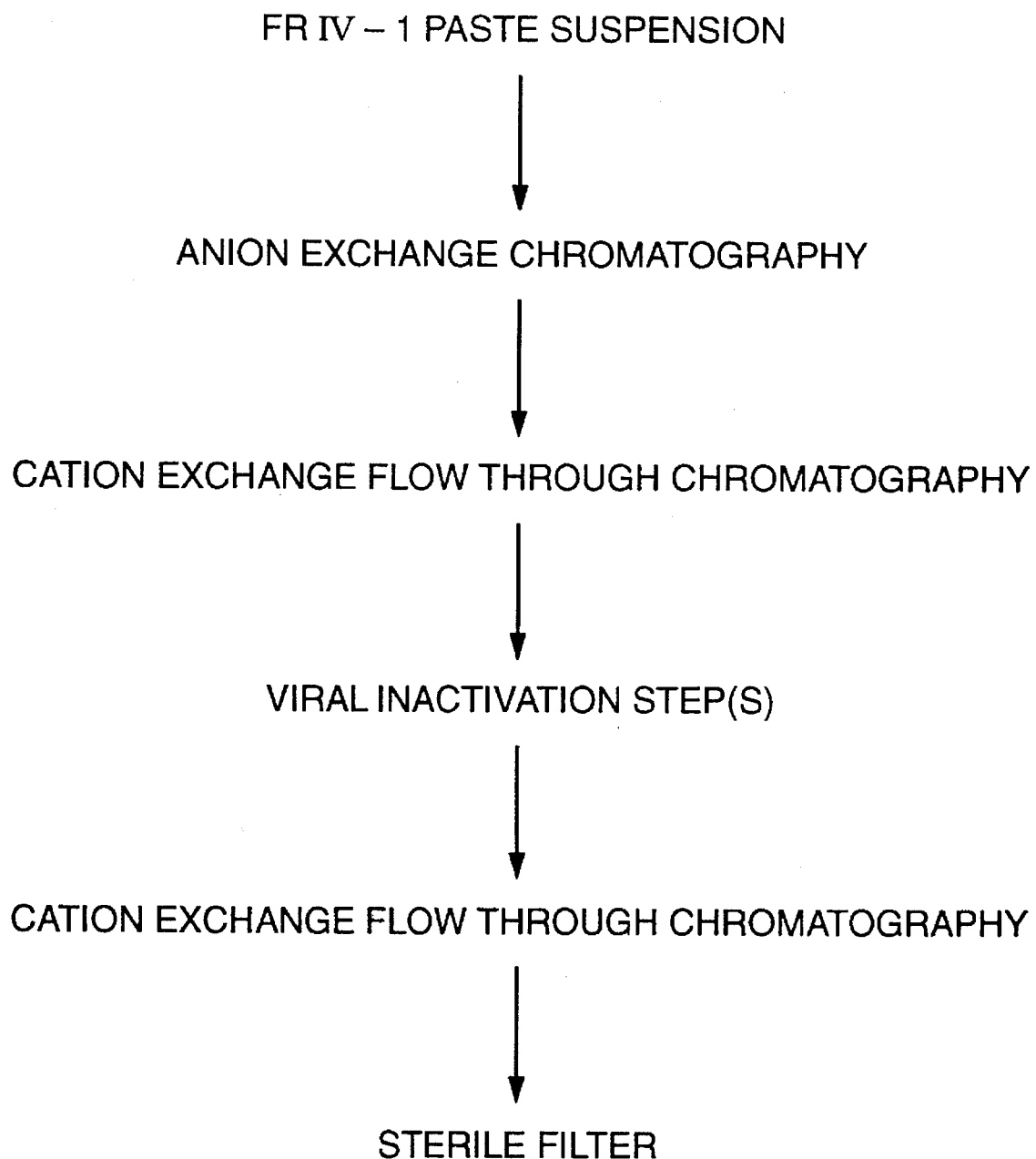
FIG._2

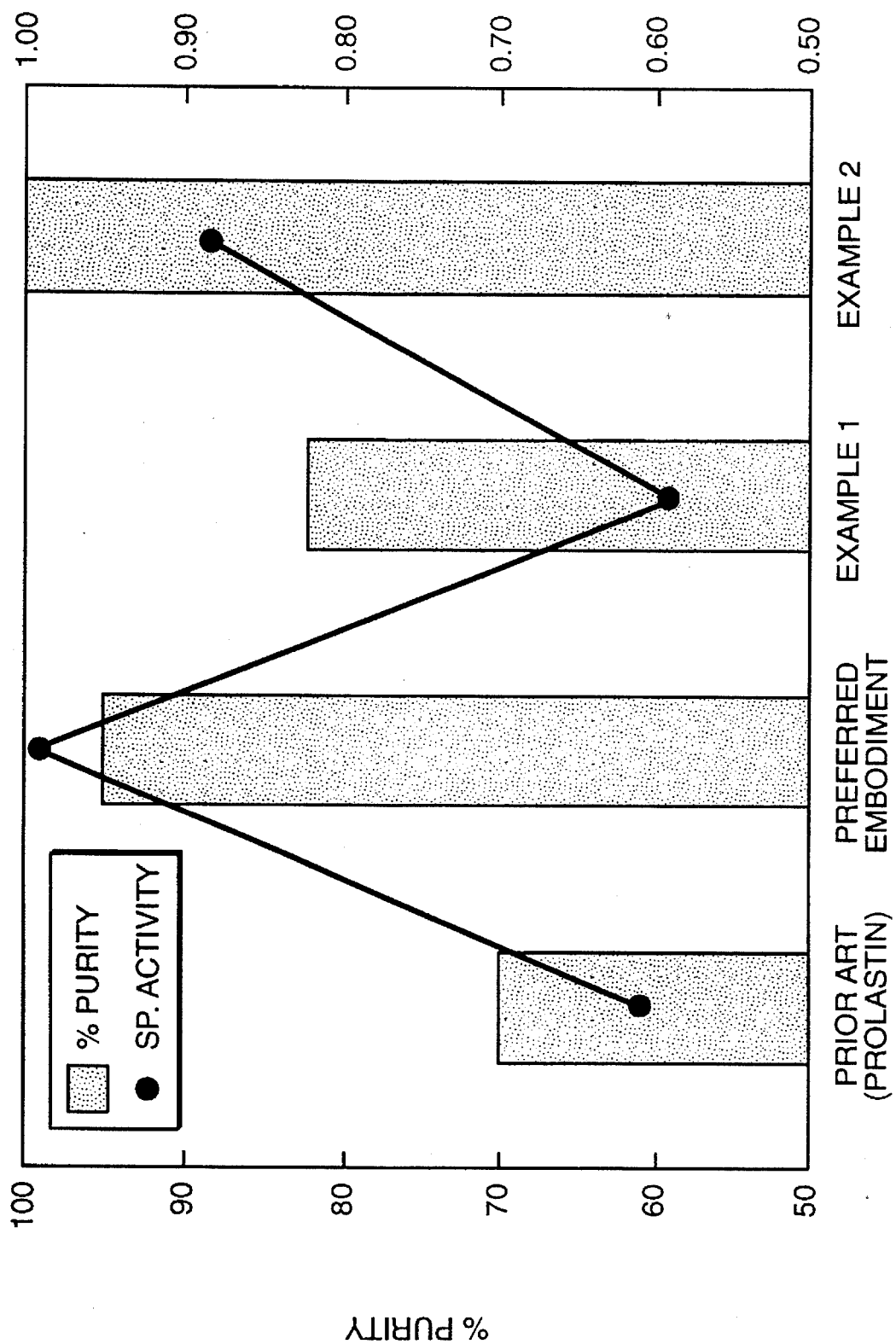
FIG._3

PURIFICATION OF α-1 PROTEINASE INHIBITOR USING NOVEL CHROMATOGRAPHIC SEPARATION CONDITIONS

BACKGROUND OF THE INVENTION

1. Field

This disclosure is concerned generally with protein purification and specifically with a method of purifying α-1 proteinase inhibitor from plasma fractions with cation exchange under conditions such that active α-1 PI does not bind to the column but contaminating proteins do.

2. Prior Art

Alpha-1 proteinase inhibitor (α-1 PI) is a glycoprotein with a molecular weight of about 55,000 Daltons. Alpha-1 PI is an inhibitor of proteases such as trypsin, chymotrypsin, pancreatic elastase, skin collagenase, renin, urokinase and proteases of polymorphonuclear lymphocytes. A current therapeutic use of α-1 PI is the inhibition of lymphocyte elastase in the lungs. This protease functions by breaking down foreign proteins. When α-1 PI is not present in sufficient quantities to regulate elastase activity, the elastase breaks down lung tissue. In time this imbalance results in chronic lung tissue damage and emphysema. Alpha-1 PI replenishment has been successfully used for treatment of this form of emphysema.

Currently the demand for α-1 PI exceeds the available supply. The α-1 PI gene has been transferred and expressed in microorganisms, cell lines and sheep. However, a satisfactory recombinant product has yet to be produced. Human plasma is still the only approved source of therapeutic α-1 PI. Alpha-1 PI is used for replacement therapy and is given to patients on a regular basis over extended periods of time. Because trace impurities can stimulate an immune response in patients, high purity of the product is critical to successful treatment. Plasma, the source of α-1 PI, is limited and therefore a purification process with high yield of α-1 PI is necessary. To date a practical process which gives both high yield and high purity α-1 PI has not been available.

Various methods of purifying α-1 PI from human plasma have been described. Bollen et al., U.S. Pat. No. 4,629,567 (1986) used five chromatography steps to purify the α-1 PI from yeast, *E. coli* and human plasma. The five steps involved DEAE ion exchange, thiol-disulfide exchange, heparin affinity, zinc-chelate chromatography, and amino hexyl ion exchange. No purity and yield data were shown.

Novika et al., *Gematol. Transfuziol.* 34:46–50(1989) reported isolation methods from the by-products of the manufacture of blood products. They used affinity, DEAE cellulose, and gel filtration chromatographies. The purity and yield data were not available.

Podiarene et al., *Vopr. Med. Khim.* 35:96–99(1989) reported a single step procedure for isolation of α-1 PI from human plasma using affinity chromatography with monoclonal antibodies. Alpha-1 PI activity was increased 61.1 fold with a yield of 20%.

Burnouf et al., *Vox. Sang.* 52, 291–297(1987) starting with plasma supernatant A (equivalent to Cohn Fraction II+III) used DEAE chromatography and size exclusion chromatography to produce an α-1 PI which was 80–90% pure (by SDS-PAGE) with a 36-fold increase in purity. Recovery was 65–70% from the supernatant A.

Hein et al., *Eur. Respir. J.* 9:16s–20s (1990) presented a process which employs Cohn Fraction IV-1 as the starting material and utilized fractional precipitation with polyethylene glycol followed by anion exchange chromatography on DEAE Sepharose®. The final product has a purity of about 60% with 45% yield.

Dubin et al., *Prep. Biochem.* 20:63–70 (1990) have shown a two step chromatographic purification. First α-1 PI, CI inhibitor, α-1 antichymotrypsin, and inter α-1 trypsin inhibitor were eluted from Blue Sepharose® and then α-1 PI was purified by gel filtration. Purity and yield data were not available.

Ballieux et al. purified an α-1 PI and proteinase-3 complex from purulent sputum using 4-phenylbutylamine affinity chromatography, cation exchange, and a final immunoaffinity step (Ballieux, B. E. et al., *J. Immunol. Methods* 159:63–70 (1993)). The pH of the buffer used in the cation exchange step was 7.0. Under the conditions used, most of the sputum proteins bound to the resin but α-1 PI and proteinase-3 passed through without binding.

Jordan et al., U.S. Pat. No. 4,749,783 (1988) described a method where biologically inactive proteins in a preparation were removed by affinity chromatography after a viral inactivation step. The basis of the separation between the native and denatured forms of the protein was the biological activity of the native protein towards the affinity resin and not physical differences between the native and denatured proteins.

None of these processes have used flow through chromatography with strong cation resins at low pH, low salt concentration and moderate protein concentration as a purification step. Unexpectedly, under conditions such as these, only active α-1 PI flows through the column. The process can be arranged to achieve 90% yield from the chromatography column and around 95% purity after 2 applications of the cation exchange column. The present invention provides an improved process for purification of α-1 PI from human plasma at large scale with both high purity and high yield.

Definition of Terms

"Active α-1 PI" or "native α-1 PI" means α-1 PI exhibiting inhibition of elastase activity in an in vitro elastase assay.

"Inactive α-1 PI" or "denatured α-1 PI" means α-1 PI which has no effect on elastase activity in an in vitro elastase assay.

"Highly purified" means containing less than 20% contaminating protein.

"Substantially free of inactive α-1 PI" means containing less than 10% inactive α-1 PI.

"Substantially free of inactive viruses" means having a reduced active virus content due to having been subjected to a recognized viral inactivation step (e.g., pasteurization or chemical treatment). In general, this means a reduction of a model virus titer of at least about 4 logs.

All conductivity measurements are determined at 25° C.

SUMMARY OF THE INVENTION

The invention is a process for purifying α-1 PI from aqueous protein-containing solutions by flow-through chromatography on cation exchange chromatography media under conditions of pH, ionic strength and protein concentration sufficient to assure that active α-1 PI does not bind to the media (or ion exchange resin) while other proteins, including inactive (or denatured) α-1 PI do bind to the media (or ion exchange resin). In preferred embodiments, the method includes the following steps:

(1) the protein solution is dialyzed or diafiltered to an ionic strength of about ≤10 mmho/cm;
(2) the solution pH is adjusted to about ≤6.0;
(3) the protein solution is adjusted to about ≤10 mg protein/mL;
(4) the solution is passed through a cation exchange chromatography resin; and
(5) the flow through fraction of the chromatography is collected as purified α-1 PI.

BRIEF DESCRIPTION OF THE FIGURES

FIG. 1 is a flow chart demonstrating the general Cohn Fractionation process, the proteins derived from the fractions, and two starting materials (Cohn Fraction IV-1 and Cohn Effluent II & III) for purifying the α-1 PI according to this invention.

FIG. 2 is a flow chart showing the preferred steps of our α-1 PI purification process.

FIG. 3 is a bar chart demonstrating the improvements in purity and specific activity with the method described in this application compared to the prior art.

DETAILED DESCRIPTION OF THE INVENTION

The present invention is an improved process for purification of α-1 PI from human plasma. The process involves cation exchange chromatography at pH≤6.0 in a low ionic strength buffer. The flow-through fraction is collected and contains purified α-1 PI. The cation exchange chromatography is specific for α-1 PI and can actually be used as a two step purification process directly from Cohn Fraction IV-1 suspension: a cation exchange column followed by a second cation exchange column.

The procedure is versatile enough that the cation chromatography will work on any number of starting materials, ranging from Cohn Fraction Effluent II+III, Cohn Fraction IV-1 paste (a presently preferred starting material) and purified α-1 PI, and still yield a substantially purified product.

As an option for large scale production of pharmaceutical product, a variety of additional steps, including vital inactivation may be added to optimize yield, improve viral safety, and assure regulatory compliance. These steps may include but are not limited to:
(1) Initial chromatography on a weak ion exchange resin (DEAE);
(2) Initial chromatography on a strong anion exchange resin (QAE);
(3) Viral inactivation utilizing either dry heat or pasteurization in solution;
(4) Viral exclusion filtration to remove possible viral contaminants;
(5) Chemical treatment such as solvent detergent treatment for viral inactivation; and
(6) Precipitation steps to partially purify starting material prior to cation chromatography.

pH plays a key role in ion exchange chromatography by changing the charged groups on the proteins. It alters the binding behavior of proteins to the chromatography resin, either from unbound to bound or vice versa. The strong cation resin ligand preferably used in this invention is a sulfonate group ($-SO_3^-$) attached to the resin bead either directly or linked via a short carbon-based chain. The ligand carries a negative charge through a pH range of 1–14. If the net effective surface charge of a protein is negative at a given pH, the protein will flow through the column without retardation. As a conventional rule, the protein has a negative charge if the pH of the solution is above its pI.

Two well characterized proteins in human plasma are α-1 PI and albumin which have mean pIs of 4.8 and 5.3 respectively. Both proteins should be negatively charged at pH 5.45 and should flow through the cation exchange column. Unexpectedly, these experiments show that at low salt concentration and pH 5.45, albumin and denatured (or inactive) α-1 PI bind to the resin and only native (or active) α-1 PI flows through the column. This observation with α-1 PI suggests that not only the pI of the protein but also its tertiary structure are important in ion exchange. The native form of α-1 PI apparently presents a negatively charged surface whereas the surface of the denatured form may be more positively charged. Therefore, the denatured protein is fortuitously bound to the cation resin. The native form of α-1 PI is much more stable at higher pH's. A pH 5.45 is the lowest pH practical when considering both stability and purification of α-1 PI by cation exchange chromatography.

The equilibrium between ion exchange resins and protein solutions is influenced by the ionic strength of the solution, protein concentration, pH and the specific ligand on the resin. Yamamoto et al., *Biotechnol. Bioeng.* 25:1373–1391 (1983) presented semi-empirical equations which related the distribution coefficient as a function of the ionic strength of the solution at low protein concentration. The equation is:

$$K = A(I)^B + K_{crt}$$

where K represents the distribution coefficient, A and B represent empirical constants, I represents ionic strength of the solution and $K_{crt}$ represents distribution coefficient of the protein at high ionic strength where electrostatic interaction can be ignored. The distribution coefficients for different proteins vary at a given ionic strength. Therefore various proteins migrate at different speed under the same conditions. This applies to the protein separation in this chromatography. At the low salt concentration, the migration rates of the most of the proteins are slowed by binding to the resin during the loading step. Native α-1 PI passes through the column due to its unique surface charge properties. If the ionic strength of the flow through buffer is increased, the interaction of other proteins with the resin is modified, and a larger percentage of proteins will flow through the column. Therefore, increasing the ionic strength of the solution will reduce the purity of the α-1 PI flowing through the column.

Salt concentration also changes the pH of the eluate by reversibly exchanging the positive ion, e.g. $Na^+$, with hydrogen ions on the resin. Increasing the salt concentration causes more $H^+$ transfer from the resin to the eluate which results in decreasing eluent pH. Therefore when the initial protein solution is ultrafiltered against equilibrium buffer, the ionic strength of the loading solution should be equal to or slightly above that of the equilibrium buffer. The pH should then remain the same or decrease only slightly during the loading. If equilibrium buffer is applied as a wash after loading, it may cause an increase of the pH due to the decreasing of ionic strength. Therefore, a slightly higher ionic strength buffer may be used in the wash to maintain the pH.

As mentioned earlier, high protein concentration also affects the equilibrium of bound protein to resin. When the protein concentration increases, the adsorption isotherm usually exhibits a saturation curve (Yamamoto et al., "Ion Exchange Chromatography of Proteins", 1988 Chromatographic Science Series) Therefore as the saturation level for binding is approached, the net quantity of impurities bound reaches a maximum. After that maximum is reached, the relative percentage of impurities passing through the column will increase as the protein concentration of the sample increases. Therefore, the protein concentration is optimum when low enough to fall into the linear range of the adsorption curve for impurities.

Because proteins tend to buffer the pH of the solution, the protein concentration also affects the pH of the eluate. As proteins are selectively removed from the solution by binding to the chromatography media, the net buffering of the solution (i.e., pH) is altered. The effect on the chromatography is complex because the pH change will depend on the relative percentages of proteins being adsorbed to the column. Adsorption is affected by the flow stream of the column, buffering capacity of the solution, the altered nature of the protein mix, and competitive binding of various proteins.

Our experiments have shown that loading a cation exchange column with higher protein concentrations results in a progressive increasing of pH in the eluate as the loading of the cation exchange column proceeds. The elevated pH results in decreased purity of α-1 PI. In order to maximize loading of the cation exchange column for large-scale purification, higher concentrations may be used within the acceptable range of the impurity curve and pH effect though, as a general principle, more dilute solutions of proteins are better starting material for α-1 PI purification chromatography.

EXAMPLE 1

Preferred Embodiment

In our presently preferred embodiment, anion exchange chromatography is used to partially purify the α-1 PI from a Cohn Fraction IV-1 (Fr. IV-1) suspension before loading onto the strong cation exchange column. Cohn Fraction IV-1 suspension is approximately 10% α-1 PI by specific activity. The IV-1 suspension, like other plasma fractions, contain various proteins: lipoprotein, immunoglobulins, globulin, metaprotein, etc. Lipoproteins present a special problem. If they bind to the chromatography resin, they are difficult to remove and can block the pores of the resin causing increased pressure across the resin bed. Also, as protein residue builds up on the resin, binding capacity is lost. To remove lipoprotein and other impurities from the Fr. IV-1 suspension, DEAE ion exchange chromatography is employed as the first step instead of the strong cation chromatography. The DEAE loading conditions are such that a major portion of the lipoproteins pass through the column without binding. Alpha-1 PI elution conditions for DEAE ion exchange chromatography are chosen based on obtaining 95–100% recovery of α-1 PI.

The IV-1 suspension is adjusted to conductivity ≧5 mmho/cm and pH 8.0. The protein solution is then loaded onto the DEAE resin. The α-1 PI is eluted with 20 mM dibasic sodium phosphate and 95 mM sodium chloride at pH 8.0. The DEAE eluate is diafiltered against 20 mM monobasic sodium phosphate and 5 mM sodium chloride at pH 6.5. The diafiltered eluent is adjusted to pH 5.45 and then loaded onto a strong cation resin. Alpha-1 PI flows through the column. The flow through is adjusted to pH 7.0 and 0.15M sodium chloride added.

At this time, the α-1 PI can be frozen if desired. For viral inactivation, the α-1 PI solution is thawed if necessary, adjusted to pH 6.5 in 60 mM histidine and 5 mM calcium chloride, and then lyophilized. The lyophilizate is then heated at 80° C. for 72 hours to inactivate viruses. The lyophilizate is then dissolved in purified water, and 37% (w/v) sucrose and 0.38M citrate are added as stabilizers. 0.3% tri-n-butyl phosphate (TNBP) and 0.2% sodium cholate are added as a solvent detergent treatment directed at enveloped viruses After 3 hours incubation at 30° C. the TNBP and cholate are removed by diafiltration.

The virally inactivated solution is diafiltered against 20 mM monobasic sodium phosphate and 5 mM sodium chloride at pH 6.5. The diafiltered solution is adjusted to pH 5.45 and loaded onto a second strong cation resin column to remove any remaining contaminants and α-1 PI denatured by the viral inactivation steps. The native form of α-1 PI flows through the column. The collected flow-through is adjusted to pH 7.0, 0.15M sodium chloride and is passed through a 15 μM filter as an additional viral inactivation step. Highly purified α-1 PI (>95%) substantially free from other proteins is produced. The DEAE chromatography removes the lipoproteins and increases α-1 PI purity to 20%. The first cation column yields about 60–70% pure α-1 PI while having a recovery of around 90%. The second cation column achieves 95% purity for the final product. The anion exchange column is washed with 1M NaCl and 1 M NaOH to remove bound proteins. The proteins bound to the two cation exchange columns are removed with 1M sodium chloride, followed by 1M sodium hydroxide.

EXAMPLE 2

In this example Cohn Fraction II+III effluent was the starting material. It was diafiltered against 20 mM monobasic sodium phosphate and 5 mM sodium chloride, pH 6.5 at 5° C. to remove alcohol and reduce the ionic strength. The solution was then adjusted to pH 5.45 and loaded onto a previously equilibrated strong cation exchange column. The flow-through was collected as a significantly enriched α-1 PI fraction. The contaminating proteins in the starting material were retained on the cation exchange column. After a single pass on the cation exchange column, α-1 PI was substantially purified from the other proteins in Cohn Fraction effluent II+III. Purity of the flow through was 82% α-1 PI by SDS-PAGE. Specific activity was increased 20 fold from 0.03 mg of elastase inhibition activity per mg total protein to 0.59 mg of elastase inhibition activity per mg protein.

EXAMPLE 3

This example used partially purified commercially available α-1 PI (Prolastin®, Miles, Inc.) as a starting material. Prolastin® is buffered in 0.1M NaCl and 0.02M sodium phosphate at pH 7.0. The concentration of α-1 PI is approximately 30 mg/mL and the protein concentration approximately 60 mg/mL. Albumin is typically 12% of the total protein and IgA is typically present at approx. 1 mg/mL (2.5% of the total protein). The Prolastin® was diafiltered with 5 mM NaCl and 20 mM monobasic sodium phosphate to reduce ionic strength. The pH of the solution was lowered to 5.45, the protein concentration reduced to 5.3 mg/mL, and the solution was run through a strong cation exchange column. The flow-through was collected as purified α-1 PI and showed only monomer and dimer PI on SDS-PAGE, 95.4% and 4.6% of the protein respectively. The solution was then stabilized at pH 7.0 in 0.15M NaCl and could be filtered or concentrated and lyophilized to give a final stable product.

The bound protein fraction was eluted and electrophoresed on SDS-PAGE. 44% of the protein visualized with Coomassie Blue was in the α-1 PI molecular weight range. The elastase inhibition assay of this fraction revealed no α-1 PI activity. This indicates that the protein in this band is inactivated α-1 PI.

The above Examples are summarized in the Table below.

| | Summary of Experimental Data | | |
|---|---|---|---|
| | Starting Material | | |
| Pretreatment | Cohn Effluent II + III Ionic strength and pH adjusted by diafiltration. Protein concentration adjusted | Cohn Fraction IV-1 Paste DEAE chromatography. Conductivity and pH adjusted by diafiltration. Protein concentration adjusted. | Prolastin (Example 3) Ionic strength and pH adjusted by diafiltration. Protein concentration adjusted. |
| Cation Column(s) Used | Macroprep High S* | Macroprep High S* (2×) | Macroprep High S* |
| Viral Clearance Step | n/a | 80° C. Dry Heat TNBP/Cholate | n/a |
| Purity by SDS-PAGE** | 82% | 95% | 100% |
| Overall Process Yield | 83% | 70% | 98%*** |
| Cation Chromatography Yield | 83% | 1st cation 94% 2nd cation 95% | 89% |
| Starting Specific Activity | 0.03 ± .003 | 0.08 ± .008 | 0.61 ± .061 |
| Final Specific Activity | 0.59 ± .059 | 0.99 ± .099 | 0.88 ± .081 |

*PerSeptive HS Resin also used successfully on lab scale.
**Percentage purity determined by Coomassie Blue stainable protein and is a combination of monomer and dimer verified by Western Blot.
***Overall yield is given post diafiltration. α-1 PI activity was observed to increase following diafiltration.

Given the above disclosure, it is thought that variations will occur to those skilled in the art of protein purification. Accordingly, it is intended that the above Examples should be construed as illustrative only and that the scope of the invention of this disclosure should be limited only to the following claims.

We claim:

1. A method of purifying alpha-1 proteinase inhibitor in an aqueous solution comprising alpha-1 proteinase inhibitor and other proteins comprising the steps of
   (A) adjusting the pH, ionic strength, and protein concentration of the aqueous solution so that active alpha-1 proteinase inhibitor does not bind to a strong ion exchange resin but other proteins in the solution do bind; and
   (B) passing the solution through the ion exchange resin and collecting a flow-through that contains alpha-1 proteinase inhibitor, wherein steps (A) and (B) are performed more than once and a viral inactivation step is performed on the solution prior to the final step (A).

2. The method in claim 1 wherein the viral inactivation step comprises heating the alpha-1 proteinase inhibitor at greater than or equal to about 60° C. for greater than or equal to about 10 hours.

3. The method in claim 1 wherein said viral inactivation step comprises the addition of chemical agents.

4. The method in claim 3 wherein said viral inactivation step comprises the addition of tri-n-butyl phosphate and a detergent to the solution.

* * * * *